United States Patent
Li et al.

(10) Patent No.: US 12,215,098 B2
(45) Date of Patent: Feb. 4, 2025

(54) SOLID FORM, CRYSTALLINE FORM, AND CRYSTAL FORM A OF FXR AGONIST, AND PREPARATION METHOD AND APPLICATION THEREOF

(71) Applicant: CSPC ZHONGQI PHARMACEUTICAL TECHNOLOGY (SHIJIAZHUANG) CO., LTD., Shijiazhuang (CN)

(72) Inventors: Xiaolin Li, Shanghai (CN); Peng Li, Shanghai (CN); Haiying He, Shanghai (CN)

(73) Assignee: CSPC ZHONGQI PHARMACEUTICAL TECHNOLOGY (SHIJIAZHUANG) CO., LTD., Hebei (CN)

( * ) Notice: Subject to any disclaimer, the term of this patent is extended or adjusted under 35 U.S.C. 154(b) by 744 days.

(21) Appl. No.: 17/297,271

(22) PCT Filed: Nov. 26, 2019

(86) PCT No.: PCT/CN2019/120992
§ 371 (c)(1),
(2) Date: May 26, 2021

(87) PCT Pub. No.: WO2020/108485
PCT Pub. Date: Jun. 4, 2020

(65) Prior Publication Data
US 2022/0033391 A1 Feb. 3, 2022

(30) Foreign Application Priority Data
Nov. 26, 2018 (CN) .......................... 201811418346.8

(51) Int. Cl.
*C07D 413/14* (2006.01)
*A61P 1/16* (2006.01)

(52) U.S. Cl.
CPC .............. *C07D 413/14* (2013.01); *A61P 1/16* (2018.01); *C07B 2200/13* (2013.01)

(58) Field of Classification Search
CPC .............. C07D 413/14; A61K 31/4709; C07B 2200/13; A61P 1/16
See application file for complete search history.

(56) References Cited

U.S. PATENT DOCUMENTS 11,339,147 B2 * 5/2022 He ..................... C07D 413/14
2020/0190074 A1   6/2020 He et al.

FOREIGN PATENT DOCUMENTS

| CN | 101877966 A | 11/2010 | |
| CN | 108341822 A | 7/2018 | |
| EP | 3632910 A1 | 4/2020 | |
| KR | 20200010483 A | 1/2020 | |
| RU | 2776052 C2 | 7/2022 | |
| WO | WO-2009005998 A1 * | 1/2009 | ............... A61P 1/16 |
| WO | 2017218337 A1 | 12/2017 | |
| WO | WO-2018214959 A1 * | 11/2018 | .......... A61K 31/422 |
| WO | 2020/108485 A1 | 6/2020 | |

OTHER PUBLICATIONS

International Search Report for International Application No. PCT/CN2019/120992 mailed Mar. 3, 2020.
Written Opinion for International Application No. PCT/CN2019/120992 mailed Mar. 3, 2020.

* cited by examiner

*Primary Examiner* — Amanda L. Aguirre
(74) *Attorney, Agent, or Firm* — Lando & Anastasi, LLP

(57) ABSTRACT

Disclosed are a solid form, a crystalline form, and crystal form A of a compound of formula (I) used as an FXR agonist, and a preparation method therefor. Also comprised is an application of the compound of formula (I) in preparation of a medication for treating nonalcoholic steatohepatitis (NASH).

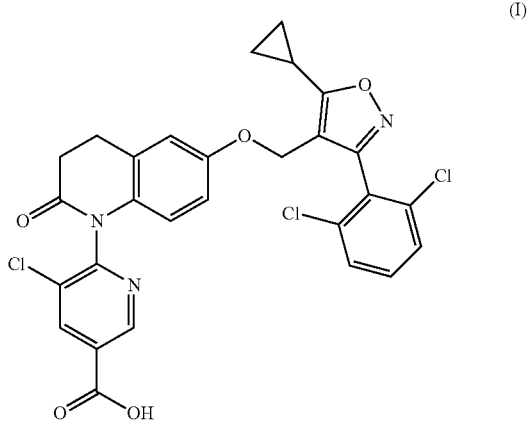

(I)

17 Claims, 3 Drawing Sheets

SOLID FORM, CRYSTALLINE FORM, AND CRYSTAL FORM A OF FXR AGONIST, AND PREPARATION METHOD AND APPLICATION THEREOF

This application is a U.S. National Stage Application under 35 U.S.C. § 371 of International Application No. PCT/CN2019/120992, filed Nov. 26, 2019, which claims the priority of CN 201811418346.8, filed on Nov. 26, 2018, the contents of each of which is incorporated herein by reference in its entirety.

FIELD OF THE INVENTION

The present disclosure relates to a solid form, a crystalline form, and a crystal form A of a compound of formula (I) as a FXR receptor agonist and a preparation method thereof, and use of the compound of formula (I) in the manufacture of a medicament for the treatment of non-alcoholic steatohepatitis (NASH).

BACKGROUND OF THE INVENTION

Farnesoid X receptor (FXR) is a member of the nuclear receptor superfamily, which was first cloned and discovered in a cDNA library of rat liver. FXR has a typical nuclear receptor structure, consisting of ligand-independent transcription activation domain, DNA binding domain, hinge region, and ligand binding region. FXR is abundantly expressed in the liver, intestine, kidney, and adrenal gland, forms a heterodimer with retinoid X receptor (RXR), and binds with DNA to modulate gene transcription. The FXR/RXR heterodimer preferentially binds to a component composed of two nuclear receptor half-sites of consensus AG(G/T)TCA organized as an inverted repeat and separated by a single nucleoside (IR-1 motif). FXR, as a bile acid-activated nuclear receptor, participates in the regulation of various physiological activities of the body, including processes such as bile acid metabolism, lipid metabolism, glucose metabolism, and liver protection and so on, and is closely associated with diseases such as metabolic syndrome, hepatobiliary disease, and type 2 diabetes and so on. Cholic acids that are endogenous ligands of FXR include chenodeoxycholic acid (CDCA), deoxycholic acid (DCA), lithocholic acid (LCA), and taurine and glycine conjugates of these cholic acids. PX104 is a FXR receptor agonist.

PX104

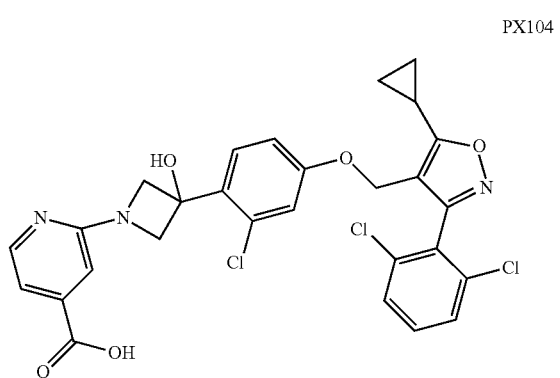 [SMILES: O=C(O)c1ccnc(N2CC(O)(c3ccc(OCc4c(-c5c(Cl)cccc5Cl)noc4C4CC4)cc3Cl)C2)c1]

SUMMARY OF THE INVENTION

The present disclosure provides a solid form of the compound of formula (I),

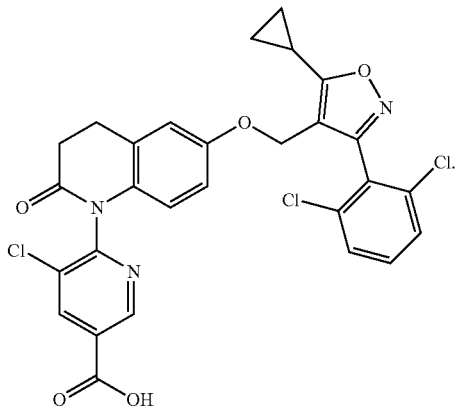

(I)

The present disclosure provides a crystalline form of the compound of formula (I).

The present disclosure provides the crystal form A of the compound of formula (I), which is characterized by X-ray powder diffraction pattern with characteristic diffraction peaks at the following 2θ angles of 3.54±0.2°, 12.72±0.2°, and 25.27±0.2°.

In some embodiments of the present disclosure, the X-ray powder diffraction pattern of the crystal form A of the compound of formula (I) as described above has characteristic diffraction peaks at the following 2θ angles of 3.54±0.2°, 11.86±0.2°, 12.72±0.2°, 16.15±0.2°, 17.40±0.2°, 19.72±0.2°, 24.18±0.2°, and 25.27±0.2°.

In some embodiments of the present disclosure, the X-ray powder diffraction pattern of the crystal form A of the compound of formula (I) as described above has characteristic diffraction peaks at the following 2θ angles of 3.54±0.2°, 11.86±0.2°, 12.72±0.2°, 16.15±0.2°, 17.40±0.2°, 19.72±0.2°, 20.38±0.2°, 22.60±0.2°, 23.80±0.2°, 24.18±0.2°, and 25.27±0.2°.

In some embodiments of the present disclosure, the X-ray powder diffraction pattern of the crystal form A of the compound of formula (I) as described above has characteristic diffraction peaks at the following 2θ angles of 3.54±0.2°, 11.86±0.2°, 12.72±0.2°, 13.67±0.2°, 16.15±0.2°, 17.40±0.2°, 19.72±0.2°, 20.38±0.2°, 22.60±0.2°, 23.80±0.2°, 24.18±0.2°, 25.27±0.2°, and 26.57±0.2°.

In some embodiments of the present disclosure, the crystal form A of the compound of formula (I) as described above has an XRPD pattern as shown in FIG. 1.

In some embodiments of the present disclosure, the XRPD pattern analysis data of the crystal form A of the compound of formula (I) as described above is as shown in Table 1:

TABLE 1

| No. | 2θ Angle (°) | D-spacing (Å) | Relative intensity (%) |
|---|---|---|---|
| 1 | 3.541 | 24.9315 | 100.0 |
| 2 | 8.123 | 10.8754 | 10.9 |
| 3 | 9.861 | 8.9620 | 7.8 |
| 4 | 10.337 | 8.5502 | 14.3 |
| 5 | 11.540 | 7.6619 | 13.4 |
| 6 | 11.856 | 7.4584 | 25.5 |
| 7 | 12.724 | 6.9513 | 79.6 |
| 8 | 13.669 | 6.4727 | 16.2 |
| 9 | 16.155 | 5.4819 | 28.8 |
| 10 | 17.400 | 5.0925 | 24.5 |

TABLE 1-continued

| No. | 2θ Angle (°) | D-spacing (Å) | Relative intensity (%) |
|---|---|---|---|
| 11 | 19.722 | 4.4977 | 31.8 |
| 12 | 20.378 | 4.3544 | 23.9 |
| 13 | 21.026 | 4.2218 | 13.2 |
| 14 | 21.536 | 4.1228 | 7.9 |
| 15 | 22.605 | 3.9302 | 23.6 |
| 16 | 23.805 | 3.7348 | 20.5 |
| 17 | 24.183 | 3.6773 | 25.6 |
| 18 | 24.814 | 3.5851 | 12.6 |
| 19 | 25.267 | 3.5218 | 62.5 |
| 20 | 26.566 | 3.3525 | 19 |
| 21 | 26.843 | 3.3185 | 8.9 |
| 22 | 27.277 | 3.2667 | 16.2 |
| 23 | 28.207 | 3.1611 | 5.8 |
| 24 | 29.056 | 3.0707 | 5.2 |
| 25 | 29.801 | 2.9955 | 14.8 |
| 26 | 32.391 | 2.7617 | 5.4 |

Note:
3.541 is the baseline peak.

In some embodiments of the present disclosure, the crystal form A of the compound of formula (I) as described above has an XRPD pattern as shown in FIG. 5.

In some embodiments of the present disclosure, the differential scanning calorimetry curve of the crystal form A of the compound of formula (I) as described above has a starting point of the endothermic peak at 223.58° C.±3° C.

In some embodiments of the present disclosure, the crystal form A of the compound of formula (I) as described above has a DSC curve as shown in FIG. 2.

In some embodiments of the present disclosure, the thermogravimetric analysis curve of the crystal form A of the compound of formula (I) as described above has a weight loss of up to 0.7427%±0.2% at 111.29° C.±3° C. and up to 3.6977%±0.2% at 202.79° C.±3° C.

In some embodiments of the present disclosure, the crystal form A of the compound of formula (I) as described above has a TGA curve as shown in FIG. 3.

The present disclosure also provides a method for preparing the crystal form A of the compound of formula (I), comprising:
(a) adding the compound of formula (I) to a solvent;
(b) stirring at 30 to 50° C. for 40 to 55 hours; and
(c) centrifugating, and then volatilizing the solvent to give the crystal form A;
wherein the solvent is alcohol, tetrahydrofuran, water, acetone, acetonitrile, ethyl acetate, a mixed solvent of alcohol and water, or a mixed solvent of acetone and water.

In some embodiments of the present disclosure, the above-mentioned alcohol is selected from methanol, ethanol, isopropanol, and n-propanol.

In some embodiments of the present disclosure, the above-mentioned solvent is a mixed solvent of alcohol and water, wherein the volume ratio of alcohol to water is 1:0.6 to 1:1.5.

In some embodiments of the present disclosure, the above-mentioned solvent is a mixed solvent of alcohol and water, wherein the volume ratio of alcohol to water is 1:1.

In some embodiments of the present disclosure, the above-mentioned solvent is a mixed solvent of acetone and water, wherein the volume ratio of acetone to water is 1:1.5 to 1:2.5.

In some embodiments of the present disclosure, the above-mentioned solvent is a mixed solvent of acetone and water, wherein the volume ratio of acetone to water is 1:2.

The present disclosure also provides a preparation method of the compound of formula (I), which comprises the following steps:

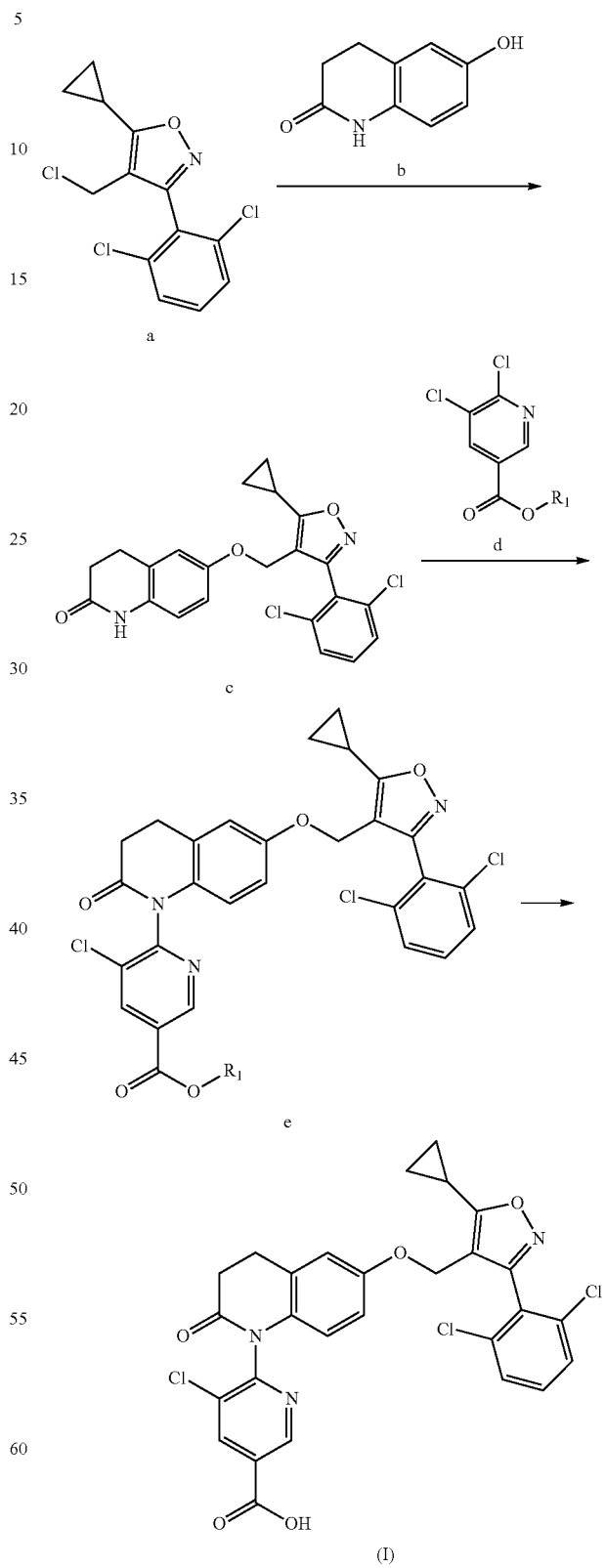

wherein $R_1$ is $C_{1-3}$ alkyl group.

In some embodiments of the present disclosure, the above-mentioned preparation method comprises the following steps:

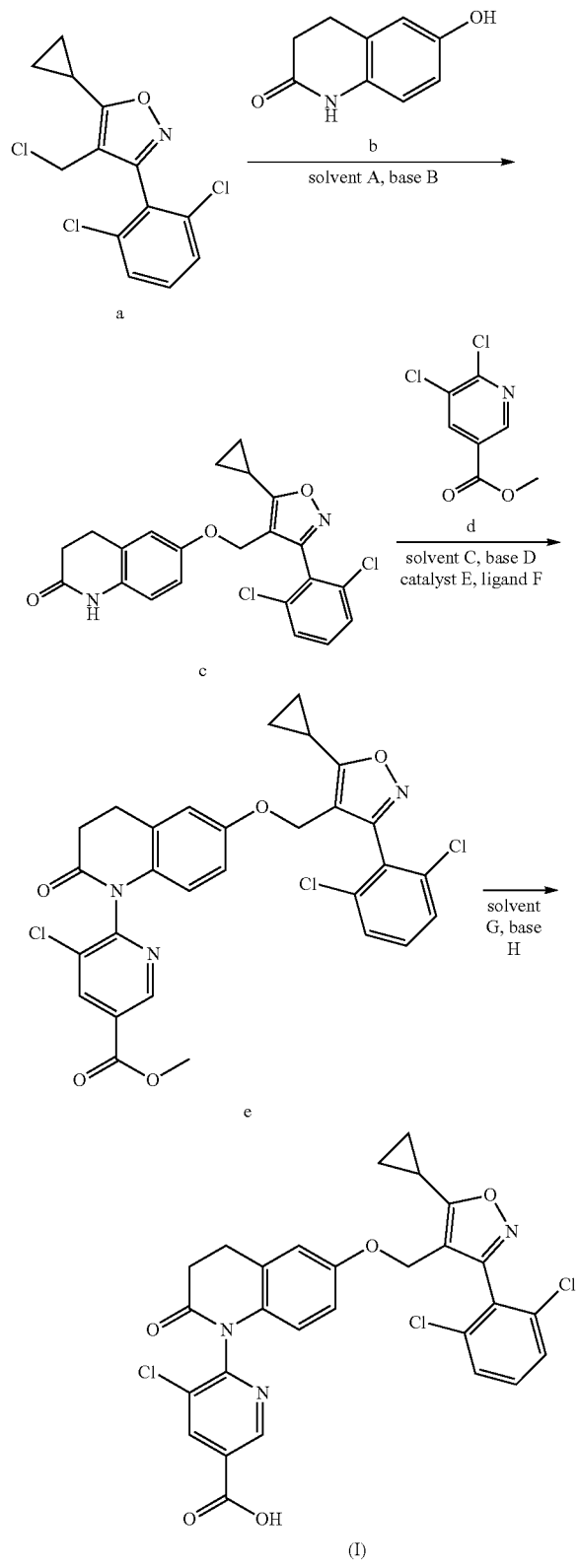

wherein,
the solvent A is DMF;
the base B is potassium phosphate;
the solvent C is toluene;
the base D is cesium carbonate;
the catalyst E is tris(dibenzylideneacetone)dipalladium;
the ligand F is 2,2-bis(diphenylphosphino)-1,1-binaphthyl;
the solvent G is tetrahydrofuran; and
the base H is sodium hydroxide.

In some embodiments of the present disclosure, in the above-mentioned preparation method, the volume:mass ratio of the solvent C to the intermediate c is 10:1, the molar ratio of the base D to the intermediate c is 2:1, the molar ratio of the catalyst E to the intermediate c is 0.025:1, and the molar ratio of ligand F to the intermediate c is 0.05:1.

The present disclosure also provides a compound represented by formula e or a pharmaceutically acceptable salt thereof,

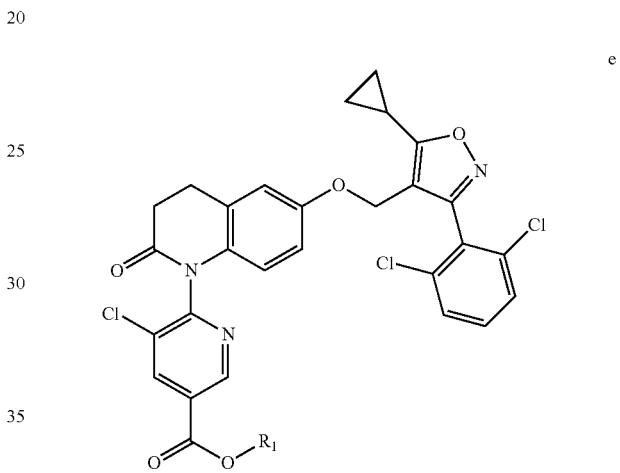

wherein $R_1$ is $C_{1-3}$ alkyl group.

In some embodiments of the present disclosure, $R_1$ is $CH_3$.

The present disclosure also provides the use of the above-mentioned solid form of the compound of formula (I) in the manufacture of a medicament for treating FXR-related diseases.

The present disclosure also provides the use of the above-mentioned crystalline form of the compound of formula (I) in the manufacture of a medicament for treating FXR-related diseases.

The present disclosure also provides the use of the above-mentioned crystal form A of the compound of formula (I) in the manufacture of a medicament for treating FXR-related diseases.

In some embodiments of the present disclosure, the above-mentioned FXR-related disease is non-alcoholic fatty liver disease.

DEFINITION AND DESCRIPTION

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The intermediate compounds of the present disclosure can be prepared by a variety of synthetic methods well known to those skilled in the art, including the specific embodiments listed below, the embodiments formed by combining the specific embodiments listed below with other chemical synthetic methods, and the equivalent alternative methods well known to those skilled in the art. The alternative embodiments include, but are not limited to, the examples of the present disclosure.

The chemical reactions in the specific embodiments disclosed herein are completed in a suitable solvent, which must be suitable for the chemical changes of the present disclosure and the reagents and materials required. In order to obtain the compound of the present disclosure, it is sometimes necessary for those skilled in the art to modify or select synthetic steps or reaction schemes based on the existing embodiments.

Unless otherwise specified, the term □$C_{1-3}$ alkyl □ is used to indicate a straight-chain or branched saturated hydrocarbon group consisting of 1 to 3 carbon atoms. The $C_{1-3}$ alkyl group includes $C_{1-2}$ and $C_{2-3}$ alkyl groups, etc. The $C_{1-3}$ alkyl group can be monovalent (such as methyl), divalent (such as methylene), or multivalent (such as methine). Examples of the $C_{1-3}$ alkyl group include, but are not limited to, methyl (Me), ethyl (Et), propyl (including n-propyl and isopropyl), and the like.

The present disclosure will be described in detail below through examples, which are not intended to limit the present disclosure.

All solvents used in the present disclosure are commercially available and can be used without further purification.

The present disclosure uses the following abbreviations: r.t. stands for room temperature; THF stands for tetrahydrofuran; NMP stands for N-methylpyrrolidone; $MeSO_3H$ stands for methanesulfonic acid; DME stands for dimethoxyethane; DCM stands for dichloromethane; Xphos stands for 2-dicyclohexylphosphino-2,4,6-triisopropylbiphenyl; EtOAc stands for ethyl acetate; MeOH stands for methanol; acetone stands for acetone; 2-Me-THF stands for 2-methyltetrahydrofuran; and IPA stands for isopropanol.

Compounds are named manually or by ChemDraw® software, and vendor directory names are used for commercially available compounds.

X-Ray Powder Diffraction (XRPD) Method Used in the Present Disclosure

Instrument model: Bruker D8 advance X-ray diffractometer

Test method: About 10 to 20 mg of sample was used for XRPD analysis.

The detailed XRPD parameters were as follows:
Light tube: Cu, kα, (λ=1.54056 Å).
Voltage of the light tube: 40 kV, electric current of the light tube: 40 mA
Divergence slit: 0.60 mm
Detector slit: 10.50 mm
Anti-scatter slit: 7.10 mm
Scanning range: 3-40 deg or 4-40 deg
Step size: 0.02 deg
Step length: 0.12 seconds
Rotation speed of sample disk: 15 rpm Differential Scanning Calorimetry (DSC) Method Used in the Present Disclosure Instrument model: TA Q2000 Differential Scanning calorimeter Test method: The sample (about 1 mg) was placed in a DSC aluminum pot for testing. Under the condition of 50 mL/min $N_2$, the sample was heated from 30° C. to 300° C. (or 350° C.) at a heating rate of 10° C./min.

Thermogravimetric Analysis (TGA) Method Used in the Present Disclosure

Instrument model: TA Q5000IR Thermogravimeter

Test method: The sample (2 to 5 mg) was placed in a TGA platinum pot for testing. Under the condition of 25 mL/min $N_2$, the sample was heated from room temperature to 350° C. or 20% weight loss at a heating rate of 10° C./min.

Dynamic Vapor Sorption (DVS) Method Used in the Present Disclosure

Instrument model: SMS DVS Advantage dynamic vapor sorption apparatus

Test condition: The sample (10 to 15 mg) was placed in a DVS sample pan for testing.

The detailed DVS parameters were as follows:
Temperature: 25° C.
Equilibration: dm/dt=0.01%/min (The shortest time: 10 min, and the longest time: 180 min)
Drying: Dried for 120 min at 0% RH
RH (%) test gradient: 10%
Range of RH (%) test gradient: 0%-90%-0%

The classification of hygroscopicity evaluation was as follows:

| Classification of hygroscopicity | ΔW % |
|---|---|
| Deliquescence | Absorb enough water and form a liquid |
| Very hygroscopic | ΔW % ≥ 15% |
| Hygroscopic | 15% > ΔW % ≥ 2% |
| Slightly hygroscopic | 2% > ΔW % ≥ 0.2% |
| No or almost no hygroscopicity | ΔW % < 0.2% |

Note:
ΔW % represents weight increase of the sample by moisture absorption at 25 ± 1° C. and 80 ± 2% RH.

Technical Effect

The crystal form A of the compound of formula (I) is stable, slightly hygroscopic, and less affected by light and heat.

The compound of formula (I) can significantly reduce the NAS score; improve inflammation and have a certain dose-dependence; significantly improve hepatic steatosis, significantly improve hepatic function and reduce hepatic damage; improve hepatic fibrosis and have a certain dose-dependence.

DETAILED DESCRIPTION OF THE INVENTION

Figure 1:
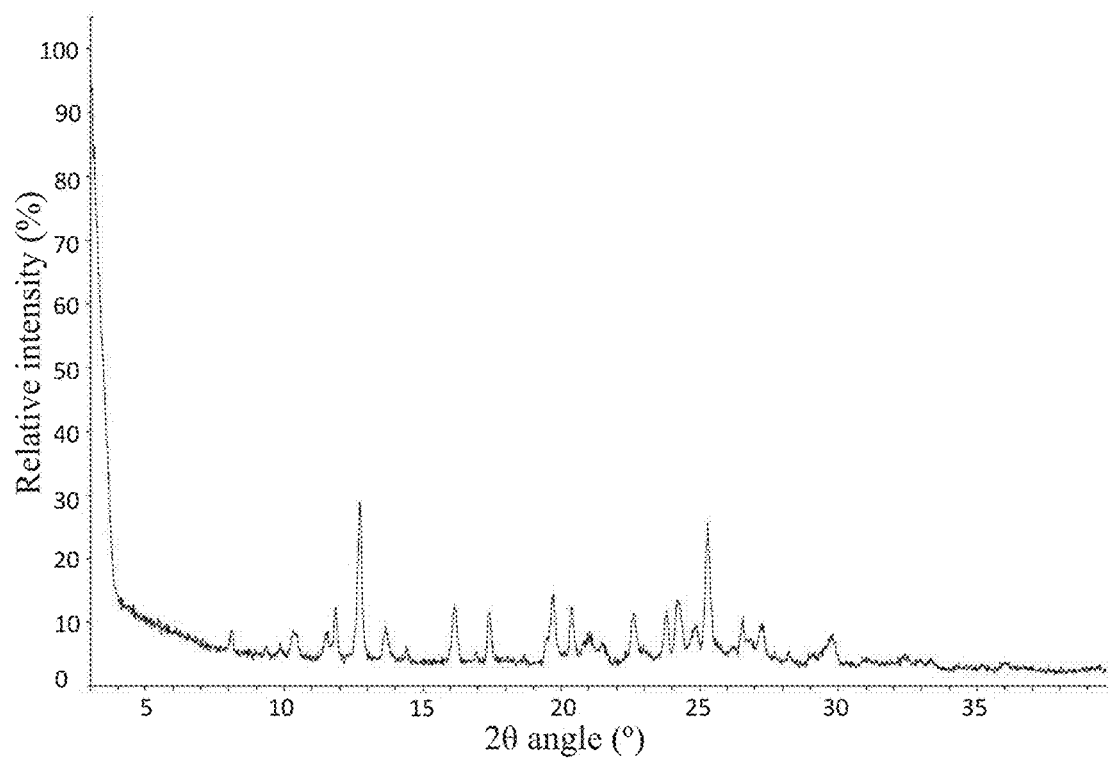
FIG. 1 is the XRPD pattern of the crystal form A of the compound of formula (I) using Cu-Kα radiation.

In order to better understand the content of the present disclosure, the present disclosure is further illustrated below in conjunction with specific examples, but the specific examples are not intended to limit the content of the present disclosure.

Example 1: Preparation of the Compound of Formula (I)

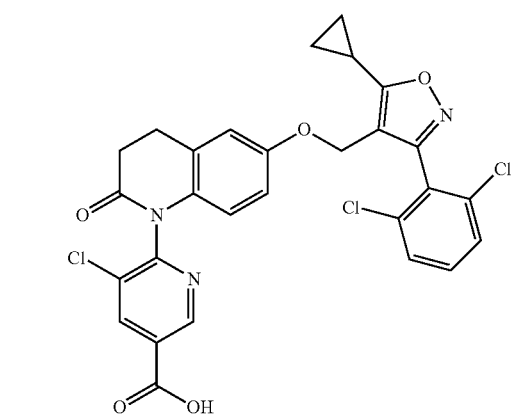

(I)

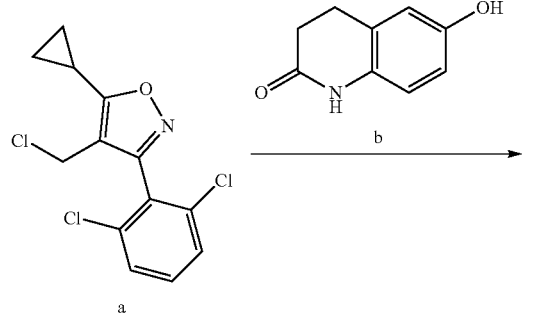

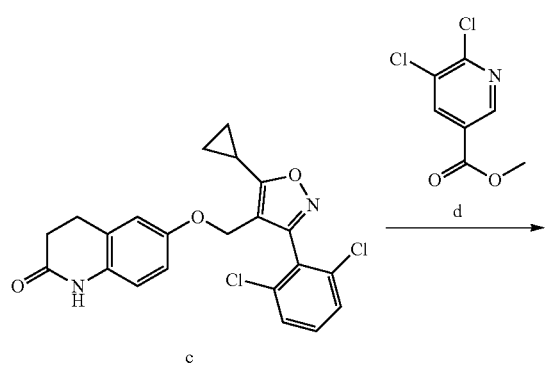

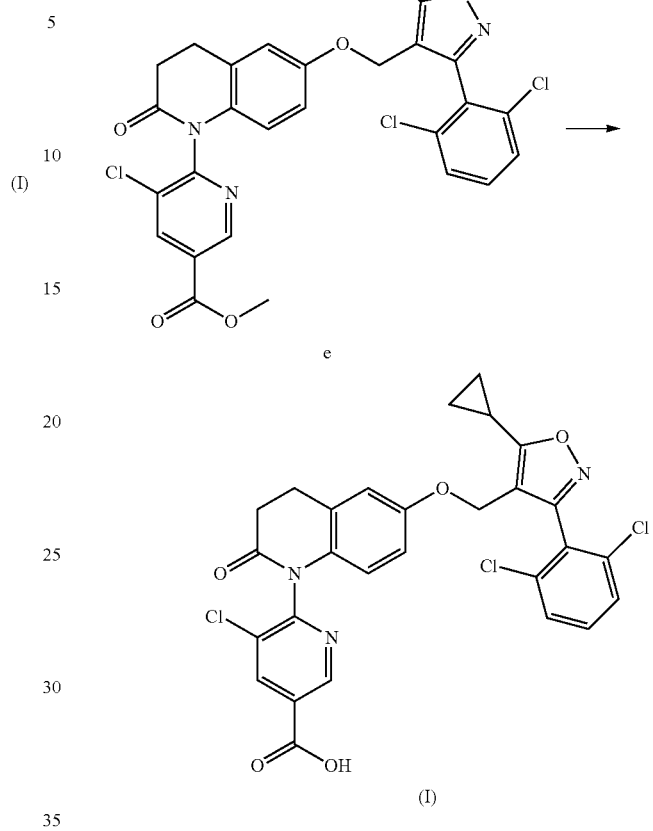

Step 1: Synthesis of the Intermediate c

The a (500.62 g, 1.65 mol) and b (323.84 g, 1.98 mol) were weighed and added to DMF (5.0 L). The mixture was stirred until clear, and then potassium phosphate (877.10 g, 4.13 mol) was added. The reaction solution was heated to 50° C. and reacted with stirring for 16 hours. The reaction solution was allowed to cool to 20° C. The reaction solution was slowly poured into water (40 L) with stirring, and a large amount of white solid precipitated out. After stirring for 15 min, the mixture was filtered, and the filter cake was rinsed with a small amount of water. The filter cake was transferred to a rotary evaporator and dried by rotary evaporation to give a crude product c (927.65 g). The crude product c (927.65 g) was added to ethanol (2.5 L). The mixture was heated to 100° C. and stirred for 1 hour. The mixture was then allowed to slowly cool to 20° C., and further stirred for 16 hours. The suspension was filtered to give a white solid. The solid was transferred to a rotary evaporator and dried by rotary evaporation to give an intermediate c (584.63 g). $^1$H NMR (400 MHz, CDCl$_3$) δ=8.62 (br s, 1H), 7.43-7.38 (m, 2H), 7.36-7.30 (m, 1H), 6.71-6.54 (m, 3H), 4.76 (s, 2H), 2.94-2.82 (m, 2H), 2.64-2.54 (m, 2H), 2.16 (tt, J=5.1, 8.5 Hz, 1H), 1.33-1.24 (m, 2H), 1.17-1.09 (m, 2H).

Step 2: Synthesis of the Intermediate e

To a 10-L three-necked reaction flask under a nitrogen atmosphere was added toluene (5.5 L). Intermediate c (551.12 g, 1.28 mol), d (396.12 g, 1.92 mol), and then cesium carbonate (834.98 g, 2.56 mol) were added at 20° C., followed by tris(dibenzylideneacetone)dipalladium (29.42 g, 32.13 mmol) and 2,2-bis(diphenylphosphino)-1,1-binaphthyl (39.98 g, 64.21 mmol). The system was heated in an oil bath with the temperature of the oil bath of 115° C., and the mixture was reacted with mechanical stirring for 48 hours. The reaction solution was allowed to cool to 20° C., and filtered through diatomaceous earth (1.0 kg). The filtrate (about 5 L) was diluted with ethyl acetate (8 L), and washed with water (6 L×2) and then saturated brine (6 L×1). The organic phase was concentrated by rotary evaporation to dryness to give a yellow oil (1.12 kg). The yellow oil (1.12 kg) was added to methanol (1.2 L) and stirred for 2 hours. A large amount of yellow solid appeared. The yellow solid was filtered, and the filter cake was rinsed with a small amount of cold methanol. The filter cake was transferred to a rotary evaporator and dried by rotary evaporation to give a crude product of intermediate e (492 g).

The above crude product of intermediate e (492 g, crude product) was suspended in 5.0 L of ethyl acetate. The system was heated in an oil bath with the temperature of the oil bath of 100° C. After stirring for 2 hours, the system became clear. The system was allowed to naturally cool to 20° C., and then a yellow solid precipitated out. The mixture was further stirred for 16 hours. The system was filtered, and the filter cake was rinsed with a small amount of ethyl acetate. The solid was dried by rotary evaporation to give a yellow solid 1 (221.56 g).

The above yellow solid 1 (221.56 g) was dissolved in 2.5 L of tetrahydrofuran, and activated carbon (110.78 g) was added. The system was stirred at 50° C. for 16 hours. The system was allowed to cool to 20° C., and then filtered through diatomaceous earth (250 g). The filtrate was concentrated by rotary evaporation to dryness to give an intermediate e (220.11 g).

LCMS (ESI): $C_{29}H_{22}Cl_3N_3O_5$ $[M+H]^+$: 597.9, 599.8

$^1$H NMR (400 MHz, CDCl$_3$) δ=9.11 (d, J=2.01 Hz, 1H) 8.49 (d, J=2.01 Hz, 1H) 7.28-7.40 (m, 3H) 6.69 (d, J=2.76 Hz, 1H) 6.50 (dd, J=8.91, 2.89 Hz, 1H) 6.03 (d, J=8.78 Hz, 1H) 4.74 (s, 2H) 3.99 (s, 3H) 2.95-3.10 (m, 2H) 2.75-2.85 (m, 2H) 2.13 (tt, J=8.41, 5.02 Hz, 1H) 1.62 (s, 1H) 1.22-1.29 (m, 2H) 1.06-1.18 (m, 2H).

Step 3

Intermediate e (220.11 g, 367.55 mmol) was dissolved in 2.5 L of tetrahydrofuran, and the solution was cooled to 5° C. A solution of sodium hydroxide (13.97 g, 349.17 mmol) in water (650 ml) was slowly added dropwise to the above system over about 40 minutes while maintaining the internal temperature at 4-8° C. The mixture was further reacted with stirring for 1 hour. 5 L of water was added to the reaction solution. The mixture was extracted with methyl tert-butyl ether (3 L×3). The solution was layered, and the organic phase was discarded. The aqueous phase was adjusted to a pH of 3-4 with 1 mol/L hydrochloric acid, and then extracted with ethyl acetate (6 L×1). The solution was layered, and the aqueous phase was discarded. The organic phase was concentrated by rotary evaporation to dryness to give 237.65 g of crude product. The crude product was added to 500 ml of acetonitrile, and stirred at 20° C. for 24 hours. The mixture was filtered, and the filter cake was rinsed with acetonitrile (200 mL). The filter cake was dried by rotary evaporation to give the compound of formula (I). $^1$H NMR (400 MHz, d$_4$-MeOH) δ=9.09 (d, J=2.0 Hz, 1H), 8.59 (d, J=2.0 Hz, 1H), 7.52-7.41 (m, 3H), 6.75 (d, J=2.8 Hz, 1H), 6.53 (dd, J=2.9, 8.7 Hz, 1H), 6.07 (d, J=9.0 Hz, 1H), 4.85 (s, 2H), 3.10-3.00 (m, 2H), 2.83-2.72 (m, 2H), 2.30 (quin, J=6.8 Hz, 1H), 1.20-1.16 (m, 4H)

Example 2: Preparation of the Crystal Form a of the Compound of Formula (I)

50 mg of the compound of formula (I) was weighed and added to a 1.5 ml high performance liquid chromatography vial. 500 μL of methanol was added respectively, and the mixture was uniformly mixed ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

50 mg of the compound of formula (I) was weighed and added to a 1.5 ml high performance liquid chromatography vial. 500 μL of ethanol was added respectively, and the mixture was uniformly mixed ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

50 mg of the compound of formula (I) was weighed and added to a 1.5 ml high performance liquid chromatography vial. 500 μL of acetone was added respectively, and the mixture was uniformly mixed ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

50 mg of the compound of formula (I) was weighed and added to a 1.5 ml high performance liquid chromatography vial. 500 μL of acetonitrile was added respectively, and the mixture was uniformly mixed ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

50 mg of the compound of formula (I) was weighed and added to a 1.5 ml high performance liquid chromatography vial. 500 μL of ethyl acetate was added respectively, and the mixture was uniformly mixed ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

50 mg of the compound of formula (I) was weighed and added to a 1.5 ml high performance liquid chromatography vial. 200 μL of tetrahydrofuran was added respectively, and the mixture was dissoved ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

50 mg of the compound of formula (I) was weighed and added to a 1.5 ml high performance liquid chromatography vial. 500 μL of water was added respectively, and the mixture was uniformly mixed or dissoved ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

50 mg of the compound of formula (I) was weighed and added to a 1.5 ml high performance liquid chromatography vial. A mixed solution (500 μL) of methanol and water with a volume ratio of 1:1 was added respectively, and the mixture was uniformly mixed or dissoved ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

50 mg of the compound of formula (I) was weighed and added to a 1.5 ml high performance liquid chromatography vial. A mixed solution (500 μL) of acetone and water with a volume ratio of 1:2 was added respectively, and the mixture was uniformly mixed or dissolved ultrasonically. The suspension sample was placed on a constant temperature shaker (40° C.) and stirred for 2 days. The dissolved sample was centrifuged at a high speed, and the supernatant was taken and added to a centrifuge tube. The tube opening was wrapped with aluminum foil paper, and small holes were punched in the aluminum foil paper. The supernatant was allowed to volatilize to give the crystal form A of the compound of formula (I).

Example 3: Study on the Hygroscopicity of the Crystal Form a of the Compound of Formula (I)

Figure 4:
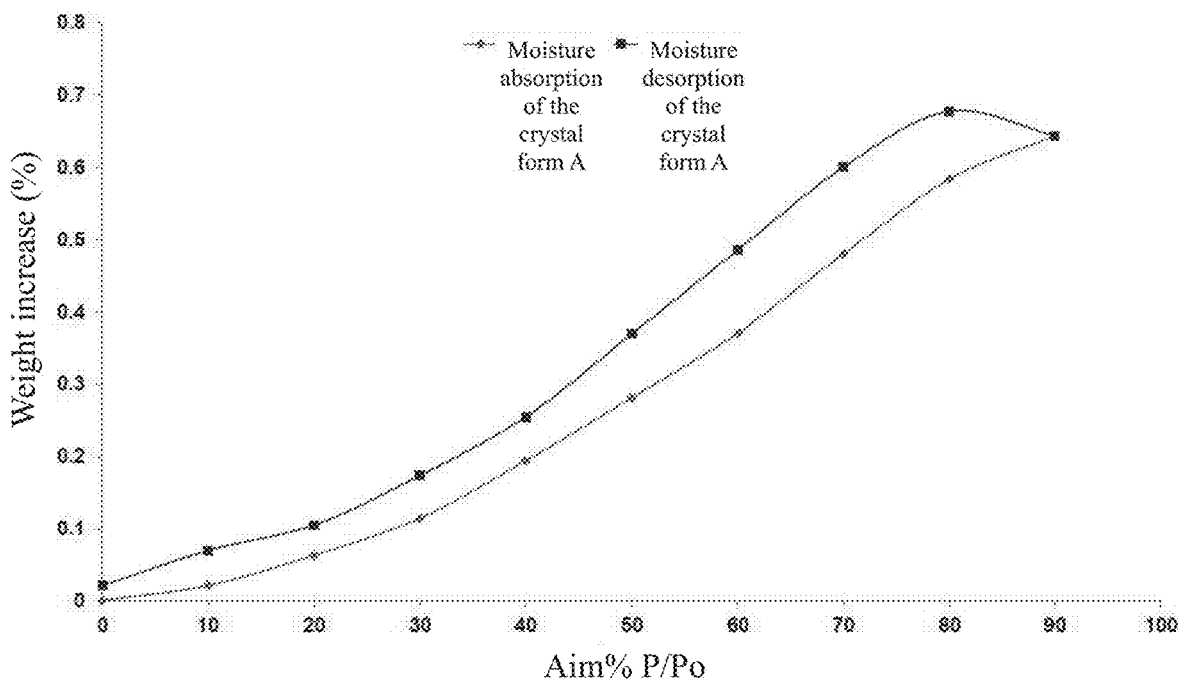
FIG. 4 is the DVS pattern of the crystal form A of the compound of formula (I)

Materials of the Assay:
SMS DVS Advantage dynamic vapor sorption apparatus
Method of the Assay:
10-15 mg of the crystal form A of the compound of formula (I) was taken and put into a DVS sample pan for testing.
Results of the Assay:
The DVS spectrum of the crystal form A of the compound of formula (I) was shown in FIG. 4, wherein ΔW is 0.5834%.
Conclusion of the Assay:
The weight increase by moisture absorption of the crystal form A of the compound of formula (I) at 25° C. and 80% RH was 0.5834%, indicating that the crystal form A of the compound of formula (I) was slightly hygroscopic.

Example 4: Solid Stability Test of the Crystal Form a of the Compound of Formula (I)

According to the "Guidelines for the Stability Testing of Drug Substances and Drug Products" (Chinese Pharmacopoeia 2015 Edition Part IV general rules 9001), the stability of the crystal form A of the compound of formula (I) was tested at high temperature (60° C., open), high humidity (room temperature/relative humidity at 92.5%, open) and strong light (5000 1x, sealed).

5 mg of the crystal form A of the compound of formula (I) was weighted and placed on the bottom of a glass sample vial to form a thin layer. For the samples placed under high temperature and high humidity conditions, the vial opening was sealed with aluminum foil paper and small holes were punched in the aluminum foil paper to ensure that the sample can fully contact the ambient air. For the samples placed under strong light condition, the vial opening was sealed with aluminum foil paper. The samples placed under various conditions were sampled and tested for XRPD on the 5th day and 10th day, and the test results were compared with the initial test results on day 0. The test results are shown in Table 2 below:

TABLE 2

Results of the solid stability test of the crystal form A of the compound of formula (I)

| Test condition | Time point | Crystal form |
| --- | --- | --- |
| — | Day 0 | Crystal form A |
| High temperature (60° C., open) | Day 5 | Crystal form A |
|  | Day 10 | Crystal form A |
| High humidity (room temperature/relative humidity at 92.5%, open) | Day 5 | Crystal form A |
|  | Day 10 | Crystal form A |
| Strong light (5000 lx, sealed) | Day 5 | Crystal form A |
|  | Day 10 | Crystal form A |

Conclusion: The crystal form A of the compound of formula (I) has good stability under conditions of high temperature, high humidity and strong light.

Example 5: In Vivo Efficacy Assay of the Compound of Formula (I)

1. Design of the Assay
The model building in this assay included two steps: high-fat diet feeding and $CCl_4$ induction. Firstly, the mice were fed with high-fat diet to induce non-alcoholic fatty liver. The mice with a body weight of >35 g were selected and continued to be fed with high-fat diet while being administered with 25% $CCl_4$ (0.5 mg/kg) by intraperitoneal injection twice a week for four weeks.

The day when the administration of $CCl_4$ was started was set as day 0, and the time when the administration of $CCl_4$ was started was set as hour 0. On the day when the administration of $CCl_4$ was started, the administration was started by intragastric gavage. The healthy control group, the model group of 1% hydroxypropyl methylcellulose (HPMC) and the PX104 control group were administered at a volume of 5 mL/kg once a day for 4 weeks (28 days), while the administration group of the compound of formula (I) and the corresponding vehicle (40% PEG400/10% solutol/50% water) model group were administered at a volume of 5 mL/kg for the first 13 days (Day 0 to Day 12) and 10 mL/kg for the next 15 days (Day 13 to Day 27), once a day. The time point of the injection of $CCl_4$ should be 4 hours or longer apart from the time point of the first administration of the day.

The assay was divided into 7 groups, namely, healthy control group, 1% HPMC model group, reference compound group (PX104), test compound group (compound of formula (I), three doses) and corresponding vehicle model group.

The healthy control group consisted of 6 normal mice, which were fed with ordinary diet during the assay, without $CCl_4$ injection.

48 obese mice were used in the model group and the administration group. Each group consisted of 8 mice. After grouping, the mice were injected intraperitoneally with $CCl_4$ and administered with different doses of drugs or vehicle, respectively.

The assay data were showed in Mean±SEM. The analysis software Graphpad Prism6 was used for comparison between two groups. T-test analysis was selected. #$p<0.05$, ##$p<0.01$, ###$p<0.001$: compared with healthy control group; *$p<0.05$, $p<0.01$, *$p<0.001$: compared with model group, PX-104 group was compared with the model group (1% HPMC) group, and the compound of formula (I) group was compared with the vehicle model group.

2. Improvement of NAS Score by the Compound of Formula (I)

For the analysis of hepatic pathology in animal models of non-alcoholic steatohepatitis, the therapeutic effect of the compound on NAFLD was comprehensively evaluated in three aspects of hepatocyte steatosis, hepatocyte ballooming degeneration, and inflammation accumulation in hepatic lobule with the reference of clinicopathological diagnosis and evaluation criteria for NAFLD, and using NAFLD activity score (NAS).

TABLE 3

Evaluation criteria for non-alcoholic steatohepatitis non-alcoholic steatohepatitis

| Pathology observed | Evaluation criteria | Score |
|---|---|---|
| hepatocyte steatosis: the area of the whole slice | <5% | 0 |
|  | 5%-33% | 1 |
|  | >33%-66% | 2 |
|  | >66% | 3 |
| hepatocyte ballooming degeneration | no | 0 |
|  | Small amount of cell swelling | 1 |
|  | Large amount of cell swelling | 2 |
| inflammation in hepatic lobule: foci of inflammation | no | 0 |
|  | <2 foci of inflammation/ 200 × field of view | 1 |
|  | 2-4 foci of inflammation/ | 2 |
| hepatocyte steatosis: the area of the whole slice | <5% | 0 |
|  | 5%-33% | 1 |
|  | >33%-66% | 2 |
|  | >66% | 3 |
|  | 200 × field of view >4 foci of inflammation/ 200 × field of view | 3 |

Compared with the healthy control group, the NAS scores of the two model groups were significantly increased ($p<0.001$); the positive control PX104 at a dose of 15 mg/kg ($p<0.001$ vs 1% HPMC model group) can significantly reduce the NAS score; compared with the vehicle model group (40% PEG400/10% solutol/50% water), the test compound of formula (I) can significantly reduce the NAS scores at test doses of 7.5 mg/kg, 15 mg/kg and 45 mg/kg. The results are shown in Table 4.

TABLE 4

NAS score

| The healthy control group | The model group (1% HPMC) | PX-104, 15 mg/kg | The vehicle model group | The compound of formula (I), 7.5 mg/kg | The compound of formula (I), 15 mg/kg | The compound of formula (I), 45 mg/kg |
|---|---|---|---|---|---|---|
| 0.0 ± 0.0 | 3.625 ± 0.255 ### | 1.479 ± 0.192 *** | 3.063 ± 0.191 ### | 1.854 ± 0.210 *** | 1.938 ± 0.249 ** | 1.188 ± 0.111 *** |

Compared with the healthy control group, the inflammation scores of the two model groups were significantly increased; the reference compound PX-104 at a dose of 15 mg/kg ($p<0.001$ vs 1% HPMC model group) can significantly improve inflammation. Compared with the vehicle model group, the test compound of formula (I) at test doses of 7.5 mg/kg, 15 mg/kg and 45 mg/kg all showed an improvement on inflammation, and had a certain dose dependence. The results are shown in Table 5.

TABLE 5

Assay of inflammation improvement

| The healthy control group | The model group (1% HPMC) | PX-104, 15 mg/kg | The vehicle model group | The compound of formula (I), 7.5 mg/kg | The compound of formula (I), 15 mg/kg | The compound of formula (I), 45 mg/kg |
|---|---|---|---|---|---|---|
| 0.0 ± 0.0 | 1.730 ± 0.151 ### | 1.000 ± 0.0 *** | 2.083 ± 0.157 ### | 1.375 ± 0.160 ** | 1.084 ± 0.063 *** | 1.043 ± 0.028 *** |

Compared with the healthy control group, the degree of steatosis in the two model groups was significantly increased; the reference compound PX-104 showed a significant improvement on hepatic steatosis at a dose of 15 mg/kg (p<0.001 vs 1% HPMC Model group). Compared with the vehicle model group, the test compound of formula (I) showed a significant improvement on hepatic steatosis at test doses of 7.5 mg/kg and 45 mg/kg. The results are shown in Table 6.

TABLE 6

Assay of hepatic steatosis

| The healthy control group | The model group (1% HPMC) | PX-104, 15 mg/kg | The vehicle model group | The compound of formula (I), 7.5 mg/kg | The compound of formula (I), 15 mg/kg | The compound of formula (I), 45 mg/kg |
|---|---|---|---|---|---|---|
| 0.0 ± 0.0 | 1.896 ± 0.134 ### | 0.479 ± 0.192 *** | 0.978 ± 0.124 ## | 0.479 ± 0.128 * | 0.854 ± 0.215 | 0.125 ± 0.088 *** |

None of mice in the assay showed hepatocyte ballooming degeneration. The results are shown in Table 7

TABLE 7

Assay of hepatocyte ballooming degeneration

| The healthy control group | The model group (1% HPMC) | PX-104, 15 mg/kg | The vehicle model group | The compound of formula (I), 7.5 mg/kg | The compound of formula (I), 15 mg/kg | The compound of formula (I), 45 mg/kg |
|---|---|---|---|---|---|---|
| 0.0 ± 0.0 | 0.0 ± 0.0 | 0.0 ± 0.0 | 0.0 ± 0.0 | 0.0 ± 0.0 | 0.0 ± 0.0 | 0.021@ ± 0.021 |

Note:
The result of 0.021@ was generated because the ballooning degeneration data of one mouse in this group was 0.17. After G test, this value was determined as an abnormal value.

3. Improvement on Hepatic Fibrosis by the Compound of Formula (I)

All slices stained with Sirius red were wholly scanned by a Digital pathoscope 4S slide scanner. 2 fields of view were randomly selected under a 5× field of view, and 2 fields of view covered 85% of the liver tissue area. Image pro-plus 6.0 software was then used for quantitative analysis, and fibrosis deposition area in the slice was calculated. Compared with the healthy control group, the degree of fibrosis in the two model groups was significantly increased (p<0.001); the reference compound PX-104 showed a significant improvement on hepatic fibrosis at a dose of 15 mg/kg (p<0.05 vs 1% HPMC model group). Compared with the vehicle model group, the test compound of formula (I) at test doses of 15 mg/kg and 45 mg/kg showed an improvement on hepatic fibrosis, and had a certain dose dependence. The results are shown in Table 8.

Conclusion:

This assay formed a typical NASH model characterized by significantly increased NAS score and apparent liver fibrosis.

The results of this assay show that the compound of formula (I) can significantly reduce the NAS score; improve inflammation and has a certain dose dependence; significantly improve hepatic steatosis, significantly improve hepatic function and reduce hepatic damage; improve hepatic fibrosis and has a certain dose dependence.

Example 6: In Vitro Biological Activity Assay of the Compound of Formula (I) FXR Biochemical Assay Purpose of the Assay:

Activation of FXR binding reaction by the compound was detected by the amplified luminescent proximity homogeneous assay (alphascreen).

Materials of the Assay:

1. Protein: Glutathione-S-transferase-labeled FXR human protein (Invitrogen)

2. Coactivator: Biotin-labeled steroid receptor coactivator (Anaspec)

3. Detection reagent: Detection kit for the amplified luminescent proximity homogeneous assay (alphascreen) (PerkinElmer)

TABLE 8

Assay of hepatic fibrosis

| The healthy control group | The model group (1% HPMC) | PX-104, 15 mg/kg | The vehicle model group | The compound of formula (I), 7.5 mg/kg | The compound of formula (I), 15 mg/kg | The compound of formula (I), 45 mg/kg |
|---|---|---|---|---|---|---|
| 1.388 ± 0.035 | 2.325 ± 0.188 ### | 1.763 ± 0.075 * | 2.821 ± 0.154 ### | 2.580 ± 0.154 | 2.350 ± 0.080 * | 2.279 ± 0.084 ** |

Method of the Assay:

1. Dilution of the compound: The test compound was prepared as a 40 μM DMSO solution, and then diluted 3-fold to 10 concentration points. The reference compound was prepared as a 400 μM DMSO solution, and then diluted 1.5-fold to 10 concentration points. The diluted DMSO solution was added to the microwells of a 384-well plate at a volume of 150 nl per well.

2. The Glutathione-S-transferase-labeled FXR human protein and the biotin-labeled steroid receptor coactivator were prepared into mixed solutions with concentrations of 0.4 nM and 30 nM, respectively. The mixed solutions were added to the microwells of the 384-well plate at a volume of 15 μL per well, and incubated for 1 hour at room temperature.

3. The mixture solution of receptor beads in the detection kit for the amplified luminescent proximity homogeneous assay (alphascreen) was diluted 125-fold, and added to the microwells of the 384-well plate at a volume of 7.5 μL per well. The operation during the assay process was protected from light. The incubation was perfomed at room temperature for 1 hour.

4. The mixture solution of donor beads in the detection kit for the amplified luminescent proximity homogeneous assay (alphascreen) was diluted 125-fold, and added to the microwells of the 384-well plate at a volume of 7.5 μL per well. The operation during the assay process was protected from light. The incubation was perfomed at room temperature for 1 hour.

5. $EC_{50}$ assay: Envision was used with excitation at 680 nm, and the absorption signal was read at 520-620 nm.

6. Analysis of the data: The data were analyzed with Prism 5.0, and the $EC_{50}$ values of the activation effect of the compound were calculated.

TABLE 9

The activation effect of the compound of formula (I) on FXR

| Compound | $EC_{50}$ (nM) Mean ± SEM |
| --- | --- |
| The compound of formula (I) | 13.85 ± 0.89 (N = 3) |
| PX-104 | 65.17 (N = 1) |

Conclusion:

The results of this assay show that the compound of formula (I) has a significant agonistic effect on FXR.

What is claimed is:

1. A crystalline form of a compound of formula (I), which is crystal form A, characterized by X-ray powder diffraction pattern with characteristic diffraction peaks at the following 2θ angles of 12.72±0.2°, and 25.27±0.2°;

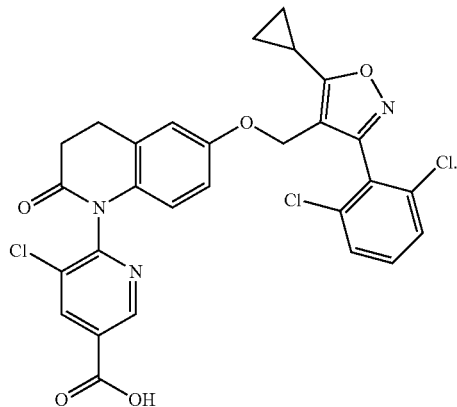

2. The crystal form A of the compound of formula (I) according to claim 1, wherein the X-ray powder diffraction pattern has characteristic diffraction peaks at the following 2θ angles of 11.86±0.2°, 12.72±0.2°, 16.15±0.2°, 17.40±0.2°, 19.72±0.2°, 24.18±0.2°, and 25.27±0.2°.

3. The crystal form A of the compound of formula (I) according to claim 2, wherein the X-ray powder diffraction pattern has characteristic diffraction peaks at the following 2θ angles of 11.86±0.2°, 12.72±0.2°, 16.15±0.2°, 17.40±0.2°, 19.72±0.2°, 20.38±0.2°, 22.60±0.2°, 23.80±0.2°, 24.18±0.2°, and 25.27±0.2°.

4. The crystal form A of the compound of formula (I) according to claim 3, wherein the X-ray powder diffraction pattern has characteristic diffraction peaks at the following 2θ angles of 11.86±0.2°, 12.72±0.2°, 13.67±0.2°, 16.15±0.2°, 17.40±0.2°, 19.72±0.2°, 20.38±0.2°, 22.60±0.2°, 23.80±0.2°, 24.18±0.2°, 25.27±0.2°, and 26.57±0.2°.

5. The crystal form A of the compound of formula (I) according to claim 4, wherein the X-ray powder diffraction pattern is as shown in FIG. 1.

Figure 5:
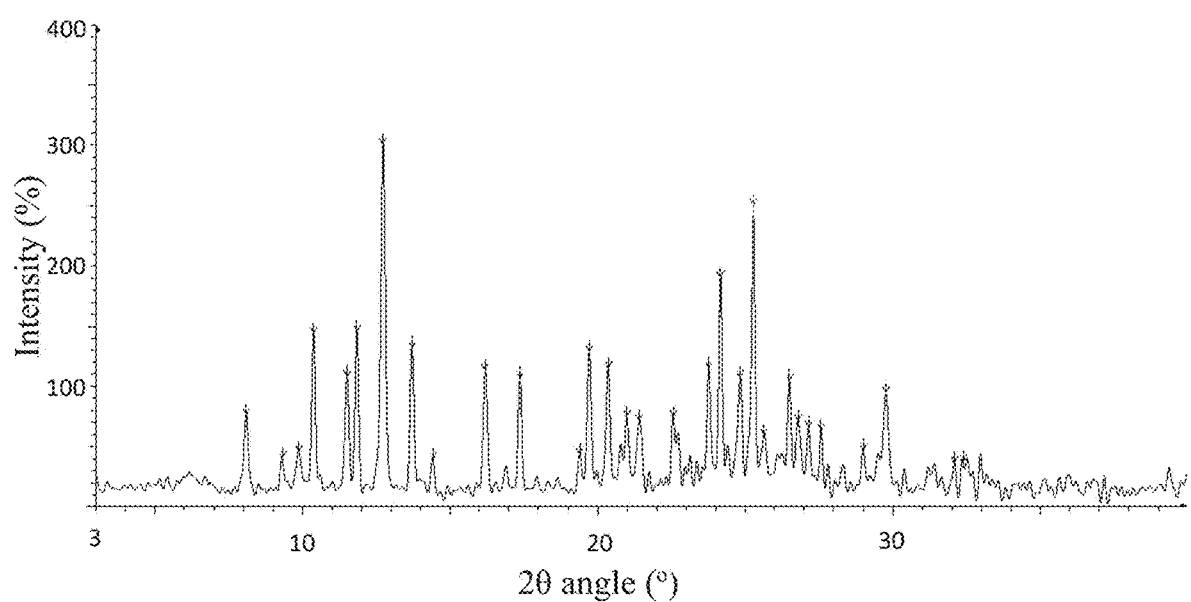
FIG. 5 is the XRPD pattern of the crystal form A of the compound of formula (I) using Cu-Kα radiation.

6. The crystal form A of the compound of formula (I) according to claim 1, wherein the X-ray powder diffraction pattern is as shown in FIG. 5.

7. The crystal form A of the compound of formula (I) according to claim 1, characterized by a differential scanning calorimetry curve having a starting point of the endothermic peak at 223.58° C.±3° C.

Figure 2:
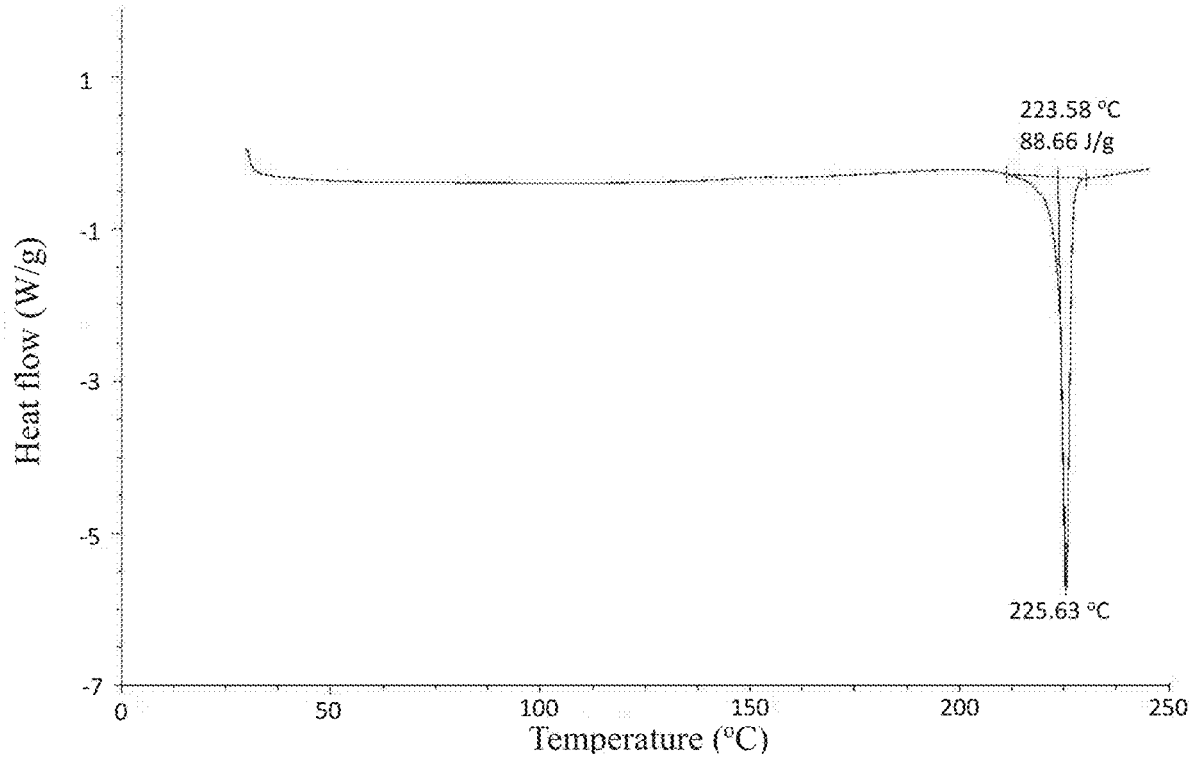
FIG. 2 is the DSC curve of the crystal form A of the compound of formula (I)

8. The crystal form A of the compound of formula (I) according to claim 7, wherein the differential scanning calorimetry curve is as shown in FIG. 2.

9. The crystal form A of the compound of formula (I) according to claim 1, characterized by a thermogravimetric analysis curve having a weight loss of up to 0.7427%±0.2% at 111.29° C.±3° C. and up to 3.6977%±0.2% at 202.79° C.±3° C.

Figure 3:
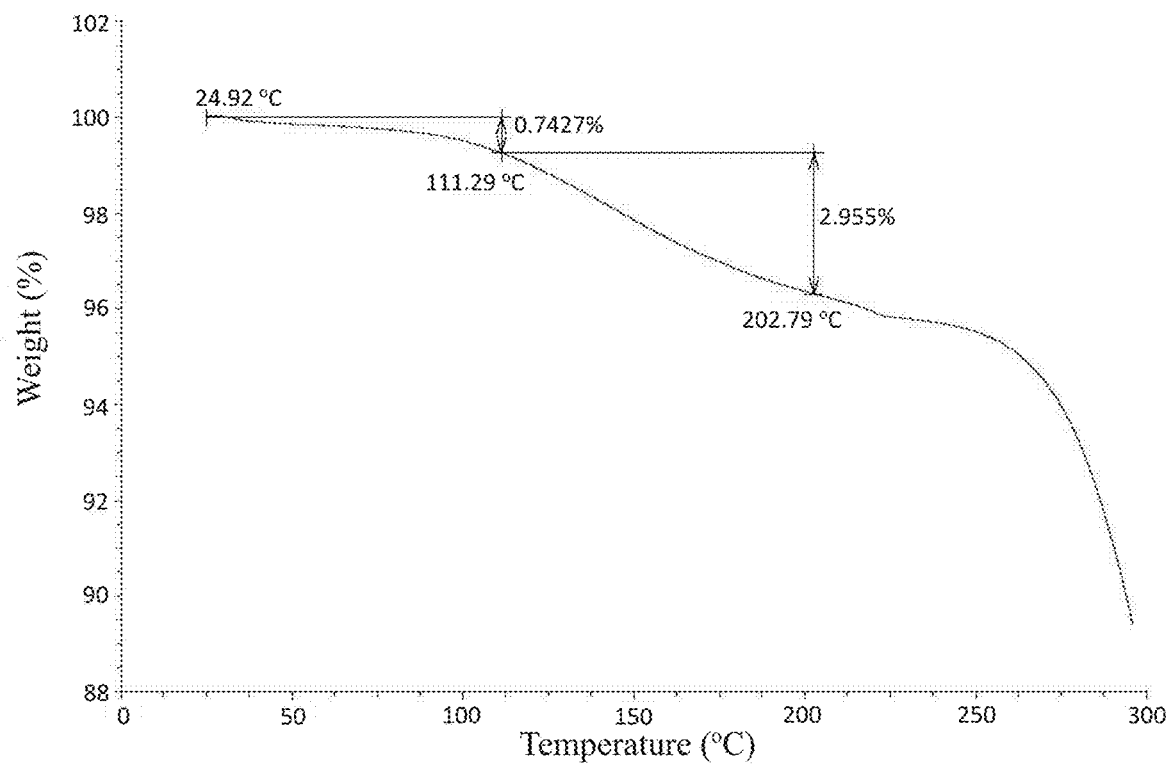
FIG. 3 is the TGA curve of the crystal form A of the compound of formula (I)

10. The crystal form A of the compound of formula (I) according to claim 9, wherein the thermogravimetric analysis curve is as shown in FIG. 3.

11. A method for preparing the crystal form A of the compound of formula (I) according to claim 1, comprising:
(a) adding the compound of formula (I) to a solvent;
(b) stirring at 30 to 50° C. for 40 to 55 hours; and
(c) centrifugating, and then volatilizing the solvent to give the crystal form A of the compound of formula (I);
wherein the solvent is alcohol, tetrahydrofuran, water, acetone, acetonitrile, ethyl acetate, a mixed solvent of alcohol and water, or a mixed solvent of acetone and water.

12. The preparation method according to claim 11, wherein the alcohol is selected from methanol, ethanol, isopropanol and n-propanol.

13. The preparation method according to claim 11, wherein the solvent is a mixed solvent of alcohol and water, wherein the volume ratio of alcohol to water is 1:0.6 to 1:1.5.

14. The preparation method according to claim 11, wherein the solvent is a mixed solvent of acetone and water, wherein the volume ratio of acetone to water is 1:1.5 to 1:2.5.

15. A method of treating a FXR-related disease selected from metabolic syndrome, hepatobiliary disease, type 2 diabetes, and non-alcoholic fatty liver disease in a subject, comprising administering to the subject the crystal form A of the compound of formula (I) according to claim 1.

16. The method according to claim 15, wherein the FXR-related disease is non-alcoholic fatty liver disease.

17. A method of improving hepatic steatosis, improving hepatic function, reducing hepatic damage, or improving hepatic fibrosis in a subject, comprising administering to the subject the crystal form A of the compound of formula (I) according to claim 1.

* * * * *